US010182767B2

(12) United States Patent
Thakur et al.

(10) Patent No.: US 10,182,767 B2
(45) Date of Patent: Jan. 22, 2019

(54) HEART FAILURE MANAGEMENT TO AVOID REHOSPITALIZATION

(71) Applicant: Cardiac Pacemakers, Inc., St. Paul, MN (US)

(72) Inventors: Pramodsingh Hirasingh Thakur, Woodbury, MN (US); Qi An, Blaine, MN (US); Barun Maskara, Blaine, MN (US); Julie A. Thompson, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/058,613

(22) Filed: Mar. 2, 2016

(65) Prior Publication Data

US 2016/0174904 A1    Jun. 23, 2016

Related U.S. Application Data

(63) Continuation of application No. 14/196,494, filed on Mar. 4, 2014, now Pat. No. 9,339,231.

(Continued)

(51) Int. Cl.
*A61N 5/02* (2006.01)
*A61B 5/00* (2006.01)
(Continued)

(52) U.S. Cl.
CPC .............. *A61B 5/7275* (2013.01); *A61B 5/02* (2013.01); *A61B 5/0205* (2013.01); *A61B 5/091* (2013.01);
(Continued)

(58) Field of Classification Search
CPC . A61B 5/0205; A61B 5/0031; A61B 5/14546; A61B 5/4839; A61B 5/7275;
(Continued)

(56) References Cited

U.S. PATENT DOCUMENTS 7,184,820 B2    2/2007 Jersey et al.
7,577,475 B2    8/2009 Cosentino et al.
(Continued)

FOREIGN PATENT DOCUMENTS

CN    101984743 A    3/2011
CN    102156818 A    8/2011
(Continued)

OTHER PUBLICATIONS

"U.S. Appl. No. 14/755,150, Non Final Office Action dated Dec. 6, 2016", 8 pgs.
(Continued)

*Primary Examiner* — Amanda K Patton
(74) *Attorney, Agent, or Firm* — Schwegman Lundberg & Woessner, P.A.

(57) ABSTRACT

Systems and methods are described for subject rehospitalization management. In an example, multiple physiologic signals can be obtained from a subject using multiple sensors. In response to a hospitalization event, pre-hospitalization characteristics of the multiple physiologic signals can be identified. Post-hospitalization characteristics of the multiple physiologic signals can be identified, including characteristics that differ from their corresponding pre-hospitalization characteristics. Later subsequent physiologic signals can be further monitored after the hospitalization event, such as using the same multiple sensors, and subsequent physiologic signal characteristics can be identified. In an example, a heart failure diagnostic indication can be determined using information about the pre-hospitalization characteristics, the post-hospitalization characteristics, and the subsequent characteristics. Information about relative changes in signal characteristics from multiple sensors can be used to identify particular subject physiologic signals to monitor during subsequent periods.

20 Claims, 6 Drawing Sheets

Related U.S. Application Data

(60) Provisional application No. 61/856,816, filed on Jul. 22, 2013, provisional application No. 61/785,451, filed on Mar. 14, 2013.

(51) Int. Cl.

| | | |
|---|---|---|
| *A61B 5/02* | (2006.01) | |
| *A61B 7/04* | (2006.01) | |
| *A61N 1/36* | (2006.01) | |
| *A61N 1/365* | (2006.01) | |
| *A61B 5/0205* | (2006.01) | |
| *A61B 5/091* | (2006.01) | |
| *A61N 1/368* | (2006.01) | |
| *G06F 19/00* | (2018.01) | |
| *A61N 1/362* | (2006.01) | |

(52) U.S. Cl.
CPC ............ *A61B 5/686* (2013.01); *A61B 5/7282* (2013.01); *A61B 5/746* (2013.01); *A61B 7/04* (2013.01); *A61N 1/3682* (2013.01); *A61N 1/36114* (2013.01); *A61N 1/36139* (2013.01); *A61N 1/36585* (2013.01); *G06F 19/00* (2013.01); *A61B 5/4848* (2013.01); *A61N 1/3627* (2013.01)

(58) Field of Classification Search
CPC ..... A61B 5/3431; A61B 5/0215; A61B 5/042; A61B 5/053; A61B 5/145; A61B 5/7239; A61B 7/00
See application file for complete search history.

(56) References Cited

U.S. PATENT DOCUMENTS

| | | | |
|---|---|---|---|
| 7,647,114 B2 | 1/2010 | Libbus | |
| 7,664,548 B2 | 2/2010 | Amurthur et al. | |
| 7,925,348 B1 | 4/2011 | Bornzin et al. | |
| 8,005,543 B2 | 8/2011 | Libbus et al. | |
| 8,052,610 B2 | 11/2011 | Bullens et al. | |
| 8,052,611 B2 * | 11/2011 | Wariar .................. | A61B 5/0031 600/508 |
| 8,303,513 B2 | 11/2012 | Wariar et al. | |
| 8,512,252 B2 | 8/2013 | Ludomirsky et al. | |
| 9,339,231 B2 | 5/2016 | Thakur | |
| 9,826,939 B2 | 11/2017 | Averina | |
| 2008/0228090 A1 | 9/2008 | Wariar et al. | |
| 2011/0009760 A1 | 1/2011 | Zhang et al. | |
| 2011/0137360 A1 | 6/2011 | Ternes et al. | |
| 2012/0253207 A1 | 10/2012 | Sarkar et al. | |
| 2012/0259183 A1 | 10/2012 | Thakur et al. | |
| 2012/0296671 A1 | 11/2012 | Simons-Nikolova et al. | |
| 2013/0131506 A1 | 5/2013 | Pollack | |
| 2013/0274705 A1 | 10/2013 | Burnes et al. | |
| 2014/0276164 A1 | 9/2014 | Thakur et al. | |
| 2016/0000380 A1 | 1/2016 | Averina et al. | |

FOREIGN PATENT DOCUMENTS

| | | |
|---|---|---|
| CN | 105228509 A | 1/2016 |
| CN | 106470598 A | 3/2017 |
| JP | 2010537767 A | 12/2010 |
| JP | 2016513533 A | 5/2016 |
| JP | 2017520380 A | 7/2017 |
| JP | 6190033 B2 | 8/2017 |
| JP | 6262405 B2 | 12/2017 |
| WO | WO-2014158800 A1 | 10/2014 |
| WO | WO-2016004009 A1 | 1/2016 |

OTHER PUBLICATIONS

"U.S. Appl. No. 14/755,150, Response filed May 2, 2017 to Non Final Office Action dated Dec. 6, 2016", 11 pgs.
"Chinese Application Serial No. 201480024185.8, Office Action dated Mar. 3, 2017", w/ English translation, 24 pgs.
"European Application Serial No. 14712460.6, Communication Pursuant to Article 94(3) EPC dated Nov. 7, 2016", 5 pgs.
"European Application Serial No. 14712460.6, Response filed Mar. 16, 2017 to Communication Pursuant to Article 94(3) EPC dated Nov. 7, 2016", 19 pgs.
"International Application Serial No. PCT/US2015/038495, International Preliminary Report on Patentability dated Jan. 12, 2017", 8 pgs.
"Japanese Application Serial No. 2016-500591, Office Action dated Sep. 13, 2016", With English Translation, 9 pgs.
"Japanese Application Serial No. 2016-500591, Response filed Feb. 28, 2017 to Office Action dated Sep. 13, 2016", w/ Claims in English, 12 pgs.
"U.S. Appl. No. 14/196,494, Notice of Allowance dated Jul. 21, 2015", 5 pgs.
"U.S. Appl. No. 14/196,494, Notice of Allowance dated Dec. 4, 2015", 7 pgs.
"International Application Serial No. PCT/US2014/020232, International Preliminary Report on Patentability dated Sep. 24, 2015", 11 pgs.
"International Application Serial No. PCT/US2014/20232, International Search Report dated May 12, 2014", 5 pgs.
"International Application Serial No. PCT/US2014/20232, Written Opinion dated May 12, 2014", 10 pgs.
"International Application Serial No. PCT/US2015/038495, International Search Report dated Sep. 14, 2015".
"International Application Serial No. PCT/US2015/038495, Written Opinion dated Sep. 14, 2015".
"Understanding Your Ejection Fraction", [Online]. Retrieved from the Internet: <ttp://my.clevelandclinic.org/heart/disorders/heartfailure/ejectionfraction.aspx>, (Accessed Apr. 18, 2013), 3 pgs.
Blair, John E, et al., "Weight changes after hospitalization for worsening heart failure and subsequent re-hospitalization and mortality in the Everest trial", European Heart Journal Jul. 2009 vol. 30, No. 13, (Jul. 2009), 1666-1673.
Damy, Thibaud, et al., "Determinants and prognostic value of pulmonary arterial pressure in patients with chronic heart failure", European Heart Journal 31, (2010), 2280-2290.
Merchant, Faisal M, et al., "Implantable Sensors for Heart Failure", Circulation: Arrhythmia and Electrophysiology 2010; 3, [Online} Retrieved from Internet: <http://circep.ahajournals.org/content/3/6/657.full>, (2010; Accessed Apr. 26, 2013), 657-667.
"U.S. Appl. No. 14/755,150, Notice of Allowance dated Jul. 28, 2017", 7 pgs.
"Chinese Application Serial No. 201480024185.8, Office Action dated Nov. 6, 2017", with translation, 22 pgs.
"Chinese Application Serial No. 201480024185.8, Response filed Jan. 19, 2018 to Office Action dated Nov. 6, 2017", w/ claims in English, 21 pgs.
"Chinese Application Serial No. 201480024185.8, Response filed Jun. 21, 2017 to Office Action dated Mar. 3, 2017", w/ claims in English, 23 pgs.
"European Application Serial No. 14712460.6, Summons to Attend Oral Proceedings mailed Aug. 18, 2017", 5 pgs.
"European Application Serial No. 14712460.6, Written Submissions filed Dec. 20, 2017 to Summons to Attend Oral Proceedings mailed Aug. 18, 2017", 16 pgs.
"European Application Serial No. 15734051.4, Response filed Aug. 10, 2017 to Communication Pursuant to Rules 161(1) and 162 EPC dated Feb. 2, 2017", 16 pgs.

* cited by examiner

HEART FAILURE MANAGEMENT TO AVOID REHOSPITALIZATION

CLAIM OF PRIORITY

This application is a continuation of U.S. application Ser. No. 14/196,494, filed Mar. 4, 2014, which claims the benefit of priority under 35 U.S.C. § 119(e) of U.S. Provisional Patent Application Ser. No. 61/785,451, filed on Mar. 14, 2013, and U.S. Provisional Patent Application Ser. No. 61/856,816, filed on Jul. 22, 2013, each of which is herein incorporated by reference in its entirety.

BACKGROUND

The heart is an electro-mechanical system performing two major pumping functions. The left side of the heart, including the left atrium and left ventricle, draws oxygenated blood from the lungs and pumps it to various organs of the body to provide the organs with oxygen for their metabolic needs. This pumped blood flow is called cardiac output. The right side of the heart, including the right atrium and right ventricle, draws deoxygenated blood from the organs and pumps it into the lungs where the blood gets oxygenated. The pumping functions are accomplished by contractions of the myocardium (heart muscles). In a normal heart, the sinoatrial node, the heart's natural pacemaker, generates electrical impulses, known as action potentials, which propagate through an electrical conduction system to various regions of the heart to excite myocardial tissues in these regions. Coordinated delays in the propagations of the action potentials in a normal electrical conduction system cause various regions of the heart to contract in synchrony such that the pumping functions are performed efficiently.

A blocked or damaged electrical conduction system causes irregular contractions of the myocardium, a condition generally known as arrhythmia. Arrhythmia reduces the heart's pumping efficiency and hence, diminishes the cardiac output. The diminished cardiac output can also be caused by heart failure, such as when the myocardium is weakened and its contractility is reduced. A heart failure subject usually suffers from both a damaged electrical conduction system and deteriorated myocardium.

Heart failure has been recognized as a significant public health concern with a huge economic impact. Subjects hospitalized with decompensated heart failure reportedly have a high rate of rehospitalization within six months (more than 50% according to some studies), with a significant percentage rehospitalized within a month. Hospital readmission is a principal factor responsible for the cost associated with managing heart failure. Premature hospital discharge and insufficient resolution of heart failure worsening are among the factors contributing to the high rate of rehospitalization. Therefore, there is a need to improve management of heart failure hospitalization for reducing the rate of rehospitalization. In an example, Wariar et al., in U.S. Pat. No. 8,052,611, entitled METHOD AND APPARATUS FOR MANAGEMENT OF HEART FAILURE HOSPITALIZATION, refers generally to a hospitalization management system.

OVERVIEW

Systems and methods are described for subject rehospitalization management. In an example, multiple physiologic signals can be obtained from a subject using multiple sensors. In response to a hospitalization event, pre-hospitalization characteristics of the multiple physiologic signals can be identified. Post-hospitalization characteristics of the multiple physiologic signals can be identified, including characteristics that differ from their corresponding pre-hospitalization characteristics. In an example, "corresponding" characteristics refers to like characteristics of a physiologic signal (e.g., peak amplitude, peak timing, etc.) obtained using the same sensor at different times. Later subsequent physiologic signals can be further monitored after the hospitalization event, such as using the same multiple sensors, and subsequent physiologic signal characteristics can be identified. In an example, a heart failure diagnostic indication can be determined using information about the pre-hospitalization characteristics, the post-hospitalization characteristics, and the subsequent characteristics.

The present inventors have recognized, among other things, that a problem to be solved can include identifying subjects at risk for rehospitalization, such as before or after discharge from a hospital or other care facility. In an example, the present subject matter can provide a solution to this problem by providing systems and methods to identify a hospitalization event, identify pre-hospitalization physiologic characteristics from a subject physiologic signal, identify post-hospitalization physiologic characteristics, from subject physiologic signals, that are different than the corresponding pre-hospitalization physiologic characteristics, and subsequently monitor the physiologic characteristics about the subject that are different than the corresponding pre-hospitalization physiologic characteristics. In an example, the same subject physiologic sensor can be used to identify the pre-hospitalization, post-hospitalization, and subsequent monitored physiologic characteristics about the subject. In an example, a heart failure parameter can be automatically determined to indicate worsening or improving heart failure status using information about the subsequently monitored characteristics relative to the pre-hospitalization or post-hospitalization characteristics.

In an example, the present subject matter can provide systems and methods to receive pre-episode physiologic signal information about a subject from one or more physiologic sensors, and, after a treatment or therapy event (e.g., a treatment or therapy event provided in response to an episode), receive post-therapy physiologic signal information about the subject from the same one or more sensors. In an example, the present subject matter can provide systems and methods to receive subsequent physiologic signal information using the same sensors used to collect pre-episode and post-therapy information, and update a subject therapy, such as a therapy provided by an implantable medical device. The therapy can be updated using information about the subsequent physiologic signal information relative to the pre-episode physiologic signal information and the post-therapy physiologic signal information.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals make describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
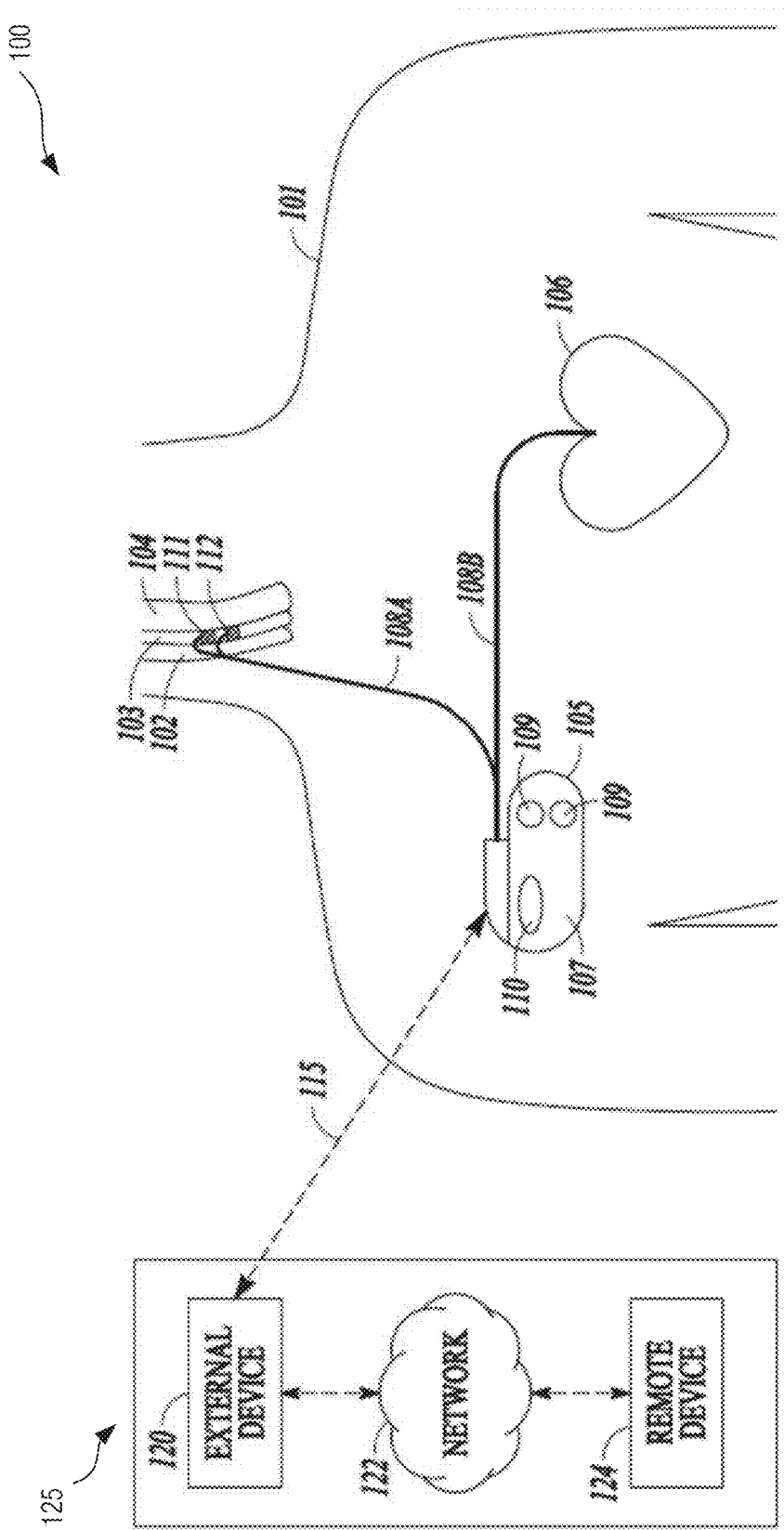
FIG. 1 illustrates generally examples of implantable and external medical systems.

Heart failure subjects are generally most vulnerable for adverse outcomes of adverse cardiac events in the first few days or weeks following discharge from a hospital or following a treatment event. Given the recent trend of reducing provider reimbursement for rehospitalization of subjects within a specified period of time following discharge (e.g., 30 days), it can be desirable to identify subjects whose health status is declining following discharge, or at other times, and to optionally initiate, adjust, or otherwise optimize one or more therapies available to the subject, such as by updating (e.g., changing) an operating characteristic of an implantable medical device.

In an example, subjects with declining or unchanging health status can be identified. For example, subjects who exhibit symptoms of worsening heart failure can be identified. In an example, one approach to identify such subjects includes tracking those aspects of a subject's clinical status or physiology that change more than others during a subject therapy period, such as to determine if those aspects revert or otherwise change.

In an example, a subject is monitored by multiple sensors, such as before, during, or after a therapy event (e.g., a hospitalization event, clinical treatment, drug administration, etc.). Signals from some sensors may change more than others, such as between an identified adverse event (e.g., an episode on-set or hospitalization period) and discharge. Such change can indicate a treatment effect on the subject. For example, a subject admitted for heart failure can be treated with diuretics. If the treatment is effective, the subject may lose weight over the course of treatment. Accordingly, the subject's weight change is an indication of the treatment effect on the subject.

In an example, characteristic information about a subject received from some sensors (e.g., sensors of a first type, such as weight sensors, oximetry sensors, heart rate sensors, ECG sensors, vessel pressure sensors, etc.) can change more than characteristic information about the subject from other sensors (e.g., sensors of a different second type), such as in response to the same treatment or duration. In an example, the characteristic information that changes more, such as corresponding to a subset of available subject sensors, can represent an aspect of a subject clinic status or physiology that is most affected by, or responsive to, the treatment (i.e., representative of the treatment effect). In an example, the subset of sensors that receive or provide the characteristic information that changes most can be further monitored, such as following subject discharge. If the characteristic information received by the subset of sensors changes by a predetermined amount, such as toward the hospitalization values, an indication of worsening subject health status can be provided, such as to indicate that a subject treatment regimen is losing its efficacy or that the patient is relapsing and may require rehospitalization. Such indications can be used to automatically change a subject therapy provided by an implantable medical device or other medical device.

In an example, as a subject approaches heart failure or other adverse health events, subject characteristic information from multiple sensors of different types are likely to change, such as to indicate worsening heart failure. As a subject undergoes treatment, such as in a hospital or elsewhere, subject characteristic information from the sensors is generally expected to return to a baseline level at discharge. However, while some of the subject characteristic information corresponding to some sensors may return to (or trend toward) baseline values, other subject characteristic information corresponding to other sensors may not, such as depending upon the appropriateness of the treatment received by the subject, or the time course of sensor measurement responding to treatment. In an example, subject characteristic information that returns to baseline can itself be used as discharge criteria. In an example, if subject characteristic information corresponding to a subset of sensors does not return to baseline at discharge (e.g., a suboptimal discharge scenario), this information can represent a residual, or untreated portion of subject heart failure. In an example, information from the subset of sensors can be expected to gradually trend toward or return to baseline following discharge or treatment. However, if the information from the subset of sensors persists at the adverse hospitalization levels (e.g., within a predetermined amount of the difference between the baseline and hospitalization levels), then the information can indicate the subject is not sufficiently recovering and may require rehospitalization.

In an example, a subject therapy can be provided or updated to attempt to avoid subject rehospitalization. For example, when a rehospitalization alert is triggered by waning of treatment as described above, a device can be configured to iterate through programming parameters to identify a set of parameters that is optimized to halt or inhibit any further subject reversion. For example, where a set of subject physiologic sensors is used to identify a treatment effect because information from the set of sensors changed the most between hospitalization and discharge, that set of sensors is representative of the subject response to treatment. If the information from the set of sensors changes by a predetermined amount toward prior hospitalization levels, a device therapy can be automatically updated or optimized, such as to select device parameters to reverse the adverse subject health status trend. One example includes raising a lower rate limit in a CRT device, such as temporarily, to alleviate acute fluid overload.

In an example, when a rehospitalization alert is triggered by subject physiologic characteristic information lingering at hospitalization levels, a therapy can be similarly updated or optimized by adjusting a device characteristic. In an example, updating a subject therapy can include adjusting one or more of an AV delay interval, a VV delay interval, a lower rate pacing limit, an electrostimulation amplitude threshold, an LV pacing electrode configuration (i.e. using quadrapolar leads), or changing a pacing mode, such as to or from a mode that is rate-responsive or activity-responsive, or to or from a forced atrial pacing mode. Some examples of other device parameters that can be optimized can include a pacing voltage, or a pacing pulse width, or a pacing pulse shape, among others.

In an example, information from a heart sound sensor can be used, such as to update or adjust one or more device parameters. In an example, information about heart sounds, such as heart sound intervals or other characteristics, can be used to adjust vagal or other neural stimulation. Some characteristics of heart sounds that can indicate a need for vagal stimulation can include a reduced S1 amplitude, an elevated S3 amplitude, a reduced R-S2 interval, an increased R-S1 interval (pre-ejection period, or PEP), a decreased S1-S2 interval (HS ejection time), or an increased PEP/HSET ratio.

Various implantable or external systems can include subject physiologic sensors that can be used to monitor one or more subject physiologic signals. For example, FIG. 1 illustrates generally an example 100 of a subject 101 with an implantable system. The implantable system can be used to provide a subject therapy and detect or receive subject physiologic signal information, such as including impedance information, heart sound information, physiologic pulsatile signal information, or other information about the subject. In the example of FIG. 1, the implantable system includes an implantable medical device (IMD) 105. The implantable medical device 105 can be configured to be coupled to one or more of a first implantable lead system 108A and a second implantable lead system 108B. In an example, the first implantable lead system 108A is configured to interact with nerve tissue or cervical vessels in the subject body 101, and the second implantable lead system 108B is configured to interact with cardiac tissue. In an example, the IMD 105 can be configured to use subject physiologic information, such as received from multiple subject sensors, to identify a subject health status after an adverse health event and treatment. Combined cardiac and neuromodulation devices are further described in Amurthur et al., U.S. Pat. No. 7,664,548, entitled DISTRIBUTED NEUROMODULATION SYSTEM FOR TREATMENT OF CARDIOVASCULAR DISEASE, Libbus et al., U.S. Pat. No. 7,647,114, entitled BAROREFLEX MODULATION BASED ON MONITORED CARDIOVASCULAR PARAMETER, and in Libbus et al., U.S. Pat. No. 8,005,543, entitled HEART FAILURE MANAGEMENT SYSTEM, which are incorporated herein by reference in their entirety.

The IMD 105 can include a conductive housing 107 and a processor circuit 110 operably connected to one or more stimulating or sensing circuits. The IMD 105 may be configured to operate autonomously with all circuitry residing within the IMD 105, and/or may be configured to operate with one or more other devices (e.g., other IMD(s) and/or external device(s) such as a programmer or an analyzer circuit). The IMD 105 can be configured to deliver neural stimulation therapy and to communicate with a different cardiac rhythm management (CRM) device, such as a pacemaker or defibrillator, which can be configured to sense physiological parameter(s) or response(s) and provide cardiac rhythm management therapy.

In an example, the IMD 105 can include a communication circuit and antenna, or telemetry coil, such as can be used to communicate wirelessly with an external system 125 or other device. The system 100 can include one or more leadless ECG electrodes 109 or other electrodes, such as can be disposed on the housing of the IMD 105. These electrodes can be used to detect heart rate or cardiac arrhythmias, among other characteristics of a cardiac cycle. For example, information received from the leadless ECG electrodes 109 can be analyzed by the processor circuit 110 to identify features of a subject electrogram, such as to identify fiducials or points of interest on a QRS complex. In an example, a heart failure analysis module includes the IMD 105 and the external system 125. In an example, the heart failure analysis module can include one or more processor circuits, such as the processor circuit 110 in the IMD 105 or one or more other processor circuits in the external system 125 that can receive information from physiologic sensors and provide an indication of a subject health status, such as a heart failure parameter.

The external system 125 can include a remote medical device programmer or one or more other remote external modules (e.g., outside of wireless communication range of the IMD 105 antenna, but coupled to the IMD 105 using an external device, such as a repeater or network access point). The external system 125 can include a dedicated processor circuit configured to process information that can be sent to or received from the IMD 105. The information can include medical device programming information, subject data, device data, instructions, alerts, or other information. In an example, the external system 125 includes an external device 120 configured to display information (e.g., information received from the IMD 105) to a user. Further, the local programmer or the remote programmer can be configured to communicate the sent or received information to a user or physician, such as by sending an alert (e.g., via e-mail) of the status of the subject 101 or the system 100. In an example, the processor circuit 110 in the IMD 105 or another processor circuit in the external system 125 can be considered to be a portion of a heart failure analysis module.

In an example, the IMD 105 can be coupled to a first implantable lead system 108A. The first implantable lead system 108A can include at least one neural stimulation lead that can be subcutaneously implanted to position electrode (s) to stimulate a neural target in a cervical region (e.g., in a region at or near the neck) in the subject body 101. Examples of cervical neural targets include a vagus nerve, a carotid sinus nerve, a hypoglossal nerve, a glossopharyngeal nerve, a phrenic nerve, baroreceptors and the nerves that innervate and are proximate to the baroreceptors, and chemoreceptors and the nerves that innervate and are proximate to the chemoreceptors. The neural target may be on the left side (e.g. left vagus nerve), or the right side (e.g. right vagus nerve). Additionally, bilateral neural targets may be stimulated. Other neural stimulation lead(s) can include electrodes configured to stimulate neural targets outside of a cervical region. For example, an electrode can be configured to stimulate a vagus nerve near the stomach.

Implanted electrode(s) disposed proximal to or in contact with a neural target can be used to provide neural electrostimulation. A first electrode 111, such as a first nerve cuff electrode, can be disposed at the end of the neural stimulation lead. In an example, the first electrode 111 can include a nerve cuff electrode that can be sized, shaped, or otherwise configured to be disposed around a vagus nerve 103. One or more additional nerve cuff electrodes, such as a second electrode 112, can be similarly provided. In an example, neural stimulation may be provided using the first and second electrodes 111 and 112 in a bipolar configuration. In an example, neural or muscular electrical activity can be detected using the first and second electrodes 111 and 112, or an electrical response signal can be provided and/or detected using the first and second electrodes 111 and 112.

Some other vagus nerve stimulation examples can include one or more electrodes that can be sized, shaped, or otherwise configured to be fed into a vessel near the vagus nerve 103, such as for using electrodes positioned within the vessel to intravascularly stimulate the neural target. For example, a neural target can be stimulated using at least one electrode positioned internally within a jugular vein 102 or a carotid artery 104. The neural stimulation may be bipolar stimulation or unipolar stimulation, such as where the conductive housing 107 of the IMD 105 functions as an electrode.

In an example, such as shown in FIG. 1, the IMD 105 can be coupled to a second implantable lead system 108B. The second implantable lead system 108B can include a cardiac electrostimulation stimulation lead that can be subcutaneously implanted to position one or more electrodes to stimulate cardiac tissue, such as myocardial or neural cardiac tissue. In an example, the second implantable lead system 108B can include multiple atrial and ventricular leads that each includes one or more electrodes for pacing and/or cardioversion/defibrillation.

The example of FIG. 1 further includes an external system 125, and a telemetry link 115 that provides bidirectional communication between the IMD 105 and the external system 125. In an example, the external system 125 includes a programmer. In another example, as illustrated in FIG. 1, the external system 125 can be a patient management system including an external device 120 in proximity of the IMD 105, a remote device 124 in a location relatively distant from the IMD 105, and a telecommunication network 122 linking the external device 120 and the remote device 124. In an example, the external system 125 is a patient management system that allows access to the IMD 105 from a remote location, such as for monitoring subject status or adjusting a subject therapy or device parameter.

In an example, the telemetry link 115 is an inductive telemetry link. In another embodiment, the telemetry link 115 is a far-field radio-frequency (RF) telemetry link. The telemetry link 115 provides for data transmission from the IMD 105 to the external system 125. This may include, for example, transmitting real-time physiological data acquired by the IMD 105, extracting physiological data acquired by and stored in the IMD 105, extracting subject history data such as data indicative of occurrences of arrhythmias, occurrences of decompensation, and therapy deliveries recorded in the IMD 105, and extracting data indicating an operational status of the IMD 105 (e.g., battery status and lead impedance). The telemetry link 115 also provides for data transmission from the external system 125 to the IMD 105. This may include, for example, programming the IMD 105 to acquire physiological data using one or more subject sensors, programming the IMD 105 to perform at least one self-diagnostic test (such as for identifying or determining a device operational status), programming the IMD 105 to deliver at least one therapy, or instructing the IMD 105 to analyze data associated with heart failure.

In an example, at least one of the IMD 105 and the external system 125 includes a heart failure analyzer that can provide hospitalization management for a heart failure subject using at least diagnostic data acquired by the IMD 105. The heart failure analyzer can analyze subject diagnostic data for therapy monitoring, risk stratification, and discharge planning during hospitalization of a heart failure subject, and for monitoring and intervention after the hospitalization of the subject (e.g., in a post-hospitalization or post-episode mode). In some examples, at least a portion of the heart failure analyzer is provided in both the IMD 105 and the external system 125. The heart failure analyzer can be implemented using a combination of hardware and software. In some examples, each element of the heart failure analyzer, including its specific embodiments, is implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof, such as can be configured to receive or archive information about the subject received from one or more sensors.

Figure 2:
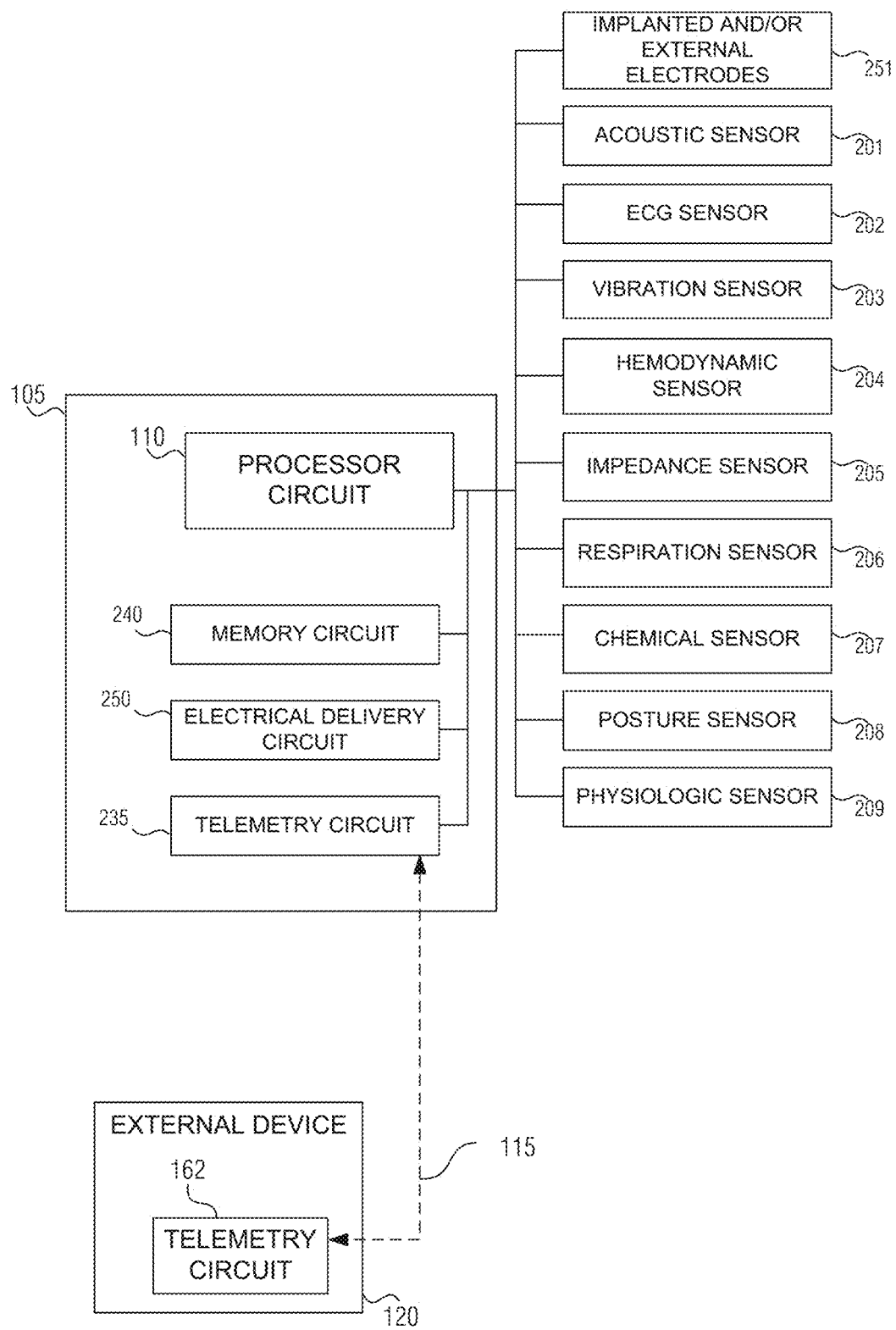
FIG. 2 illustrates generally an example of an implantable device coupled to multiple sensors.

FIG. 2 illustrates generally an example of the IMD 105. The IMD 105 includes the processor circuit 110. The IMD 105 further includes an electrical energy delivery circuit 250, such as can be configured to use a constant current or voltage source to deliver an electrical signal between two or more electrodes (e.g., using one or more electrodes included in the first or second implantable lead systems 108A and 108B), such as disposed in a cervical, thoracic, cardiac, or other body region. In an example, the electrical delivery circuit 250 is coupled to a neural electrostimulation circuit comprising implanted and/or external electrodes 251 configured to provide electrostimulation to neural targets. In an example, the electrical delivery circuit 250 is coupled to a cardiac electrostimulation circuit comprising the implanted and/or external electrodes 251 configured to provide electrostimulation in or near a subject heart. In the example of FIG. 2, a telemetry circuit 235 is connected to the processor circuit 110. The telemetry circuit 235 can transmit data from the IMD 105 to an adjunct system, such as the external device 120. Transmitted data can include, among other things, data from one or more sensors coupled to the IMD 105, diagnostic information generated by the IMD 105, or device configuration or programming information about the IMD 105.

In an example, the processor circuit 110 is coupled to one or more physiologic sensors, such as using multiple sensor data inputs. For example, a data input of the processor circuit 110 can be coupled to one or more of an acoustic sensor 201, a device-based or other ECG sensor 202, a vibration sensor 203, a hemodynamic sensor 204, an impedance sensor 205, a respiration sensor 206, a chemical sensor 207, a posture sensor 208, or other physiologic sensor 209. In an example, the processor circuit 110 is configured to calculate or derive subject physiologic information (e.g., ejection fraction, pre-ejection period, etc.) using information received from one or more of the physiologic sensors. In an example, the processor circuit 110 includes a data output configured to provide a heart failure parameter about the subject, including a quantification of a subject's worsening or improving health status.

In an example, an acoustic sensor 201 is coupled to the processor circuit 110. The acoustic sensor 201 can be an implantable or external transducer, such as a microphone or accelerometer. The acoustic sensor 201 can be configured to receive acoustic vibrational energy from a subject, such as in the audible spectrum. In an example, a portion of the processor circuit 110 can be configured to receive information from the acoustic sensor 201 and identify one or more of heart sound information, respiration information, or other physiologic information. For example, information from the acoustic sensor 201 can be used to identify an S1 heart sound timing or amplitude characteristic, or to identify a presence of an S3 or S4 heart sound.

In an example, an ECG sensor 202 is coupled to the processor circuit 110. The ECG sensor 202 can be an implantable or external sensor. For example, the ECG sensor 202 can include at least two electrodes disposed in or on the subject body 101 and configured to detect electrical activity from the subject body 101. In an example, the ECG sensor 202 includes two implanted electrodes (e.g., a can electrode and a remote electrode disposed in or on the heart 106, such as included in the second implantable lead system 108B) in the subject body 101. The processor circuit 110 can be configured to receive electrogram information from the ECG sensor 202. In an example, the processor circuit 110 can use the received electrogram information to identify morphological characteristics (e.g., timings, amplitudes, shapes, etc.) of a subject QRS complex.

In an example, a vibration sensor 203 is coupled to the processor circuit 110. The vibration sensor 203 can be an implantable or external transducer, such as an accelerometer. The vibration sensor 203 can be configured to receive vibrational energy from a subject, such as can be used to identify one or more of cardiac activity, respiratory activity, or other subject physical activity level, such as a relative exercise or exertion level. In an example, a portion of the processor circuit 110 can be configured to receive information from the vibration sensor 203 and identify one or more of heart sound information, respiration information, or other physiologic information.

In an example, a hemodynamic sensor 204 is coupled to the processor circuit 110. The hemodynamic sensor 204 can be an implantable or external pressure sensor, such as an implantable sensor configured to continuously or intermittently monitor intracardiac or vessel pressures. In an example, the hemodynamic sensor 204 can include a pressure sensor coupled to an RV or atrial lead of the IMD 105, or the hemodynamic sensor 204 can alternatively or additionally include a pressure sensor disposed in a pulmonary artery. The processor circuit 110 can be configured to receive pressure information from the hemodynamic sensor 204.

In an example, an impedance sensor 205 is coupled to the processor circuit 110. The impedance sensor 205 can be implantable or external to the subject body 101, or can include both implantable and external portions. In an example, the impedance sensor 205 includes at least two electrodes disposed in or on the subject body 101 and configured to detect responsive electrical signals from the subject body 101, such as in response to a non-tissue-stimulating electrostimulation provided to the subject body 101 using the same or different at least two electrodes. In an example, the impedance sensor 205 includes two implanted electrodes (e.g., a can electrode and a remote electrode disposed in or on the heart 106, such as included in the second implantable lead system 108B) in the subject body 101. The processor circuit 110 can be configured to receive electrical signal information from the impedance sensor 205 to identify a detected or measured impedance between the two or more electrodes. In an example, the processor circuit 110 can use the received impedance information to identify cardiac activity, respiratory activity, muscle activity, thoracic fluid level, vessel dimensional changes (e.g., using impedance plethysmography techniques), or other information about a subject physiologic status.

In an example, a respiration sensor 206 is coupled to the processor circuit 110. The respiration sensor 206 can be an implantable or external respiration sensor, such as an implantable sensor configured to monitor subject chest expansion and contraction. In an example, the respiration sensor 206 can be configured to provide information about a subject tidal volume or minute ventilation. The processor circuit 110 can be configured to receive respiratory information from the respiration sensor 206.

In an example, a chemical sensor 207 is coupled to the processor circuit 110. The chemical sensor 207 can be an implantable or external sensor configured to identify one or more biomarkers. For example, the chemical sensor 207 can be configured to detect subject chemistry information, such as including information about one or more of a subject blood chemistry (e.g., electrolytes, glucose, pH, oxygen level, carbon dioxide level, etc.), natriuretic peptides (i.e., B-type natriuretic peptide (BNP), N-terminal proBNP, atrial natriuretic peptide, etc.), inflammatory markers, oxidative stress markers, or collagen turnover or extracellular matrix peptides, among other information. The processor circuit 110 can be configured to receive subject chemistry information from the chemical sensor 207.

In an example, a posture sensor 208 is coupled to the processor circuit 110. The posture sensor 208 can be an implantable or external posture sensor configured to detect, determine, or differentiate between patient postures. For example, the posture sensor 208 can include an accelerometer configured to provide information about whether the sensor (e.g., installed in or otherwise coupled to the subject) is vertically or horizontally oriented. In an example, the posture sensor 208 includes an impedance sensor, such as configured to measure a thoracic or vessel impedance from which subject orientation can be determined. The processor circuit 110 can be configured to receive subject posture information from the posture sensor 208.

In an example, other physiologic sensors 209 can be coupled to the processor circuit 110 to receive information about a physiologic or health status of a subject.

A memory circuit 235 can be coupled to the processor circuit 110 and/or to one or more of the physiologic sensors 201-209, such as to record subject physiologic information over time. In an example, the processor circuit 110 can access subject physiologic information stored in the memory circuit 240, such as to identify changes or trends in the subject physiologic information over time. For example, heart sound amplitude information received using the acoustic sensor 201 can be stored in the memory circuit 240 and trended over time using the processor circuit 110, such as to identify increasing or decreasing heart sound amplitude over time. The processor circuit 110 can modify or otherwise process information stored in the memory circuit 240, such as to transform one or more physiologic signals. For example, the processor circuit 110 can be configured to generate, for example, one or more of a derivative waveform, a filtered waveform, or an integrated waveform of an impedance signal sensed by the impedance sensor 205. Such transformation can be implemented with, for example, a differentiator, a filter (e.g., linear, high pass, low pass, band pass), a derivative circuit, or an integrator circuit, among others, such as can be integrated with or coupled to the processor circuit 110.

In an example, the systems described above in the discussion of FIGS. 1 and 2, such as including the external system 125 and the IMD 105, among other systems, can be used to monitor or receive physiologic signals from a subject using one or more subject physiologic sensors. The external system 125 or the IMD 105 can be configured to identify or receive an indication of a hospitalization event or indication of some other adverse subject health episode (herein generally referred to as a "hospitalization event"). In response to the hospitalization event, or before the hospitalization event, the processor circuit 110 (or a similar processor in a portion of the external system 125) can be configured to identify, in one or more received physiologic signals, pre-hospitalization physiologic signal characteristics. In some examples, pre-hospitalization can also include "at arrival" to a hospitalization event. In some situations, the information for the pre-hospitalization period may be limited to the data available when the subject is identified with worsening heart failure or other condition, such as when a subject first contacts a caregiver, or first arrives at a hospital or other treatment facility. In this example, the initial measurement at the time of hospitalization can be considered and used as information corresponding to the pre-hospitalization period.

In an example, the processor circuit 110 can be configured to receive an impedance signal from the impedance sensor 205 before the hospitalization event, and the processor circuit 110 can be configured to identify one or more characteristics of the impedance signal (e.g., a peak amplitude, a peak timing, a peak change timing, an amplitude at a particular time point within a cardiac cycle, an average impedance over a predetermined duration, a thoracic fluid level estimate, etc.) during the pre-hospitalization period. In this example, the processor circuit 110 can be configured to receive the same or different impedance signal (e.g., using the same electrodes) during a "post-hospitalization" period. In an example, the post-hospitalization period includes a duration following the hospitalization event when a subject is at a hospital or undergoing a treatment. Following treatment during the post-hospitalization period, a subsequent period can include a period after the subject is discharged from the hospital or after the subject has undergone a particular therapy or device modification. For example, during the post-hospitalization period, one or more operating characteristics of a subject's IMD can be adjusted (e.g., an AV delay in a CRT device is decreased, or a lower rate limit is increased), and during the subsequent period, one or more physiologic signals from the subject can be monitored to identify subject characteristics that change (or do not change) in response to the IMD adjustment.

In an example, information about the changed and unchanged subject characteristics can be used to determine a heart failure parameter for the subject, such as using the processor circuit 110 (or another processor circuit, such as included in the external system 125). In an example, the heart failure parameter is provided using information about a subsequent physiologic signal characteristic relative to its corresponding pre-hospitalization physiologic signal characteristic. In an example, the heart failure parameter is an indication of an overall subject health status, such as can be used to provide a discharge recommendation.

In an example, the heart failure parameter can be used to identify worsening heart failure and, depending on the sensors used to determine the heart failure parameter, various subject therapies can be implemented or changed, such as automatically by the processor circuit 110. In an example, in response to the heart failure parameter indicating worsening heart failure, a lower rate limit of the IMD 105 can be raised, such as temporarily to alleviate symptoms. In an example, in response to worsening heart failure, a pacing amplitude or pacing waveform shape can be changed. For example, an amplitude can be increased, or a duration of one or both portions of a biphasic waveform can be increased or decreased. In an example, in response to worsening heart failure, an electrostimulation application location can be changed. For example, using a multipolar lead, different combinations of electrodes (e.g., corresponding to a left ventricle) can be selected.

Figure 3:
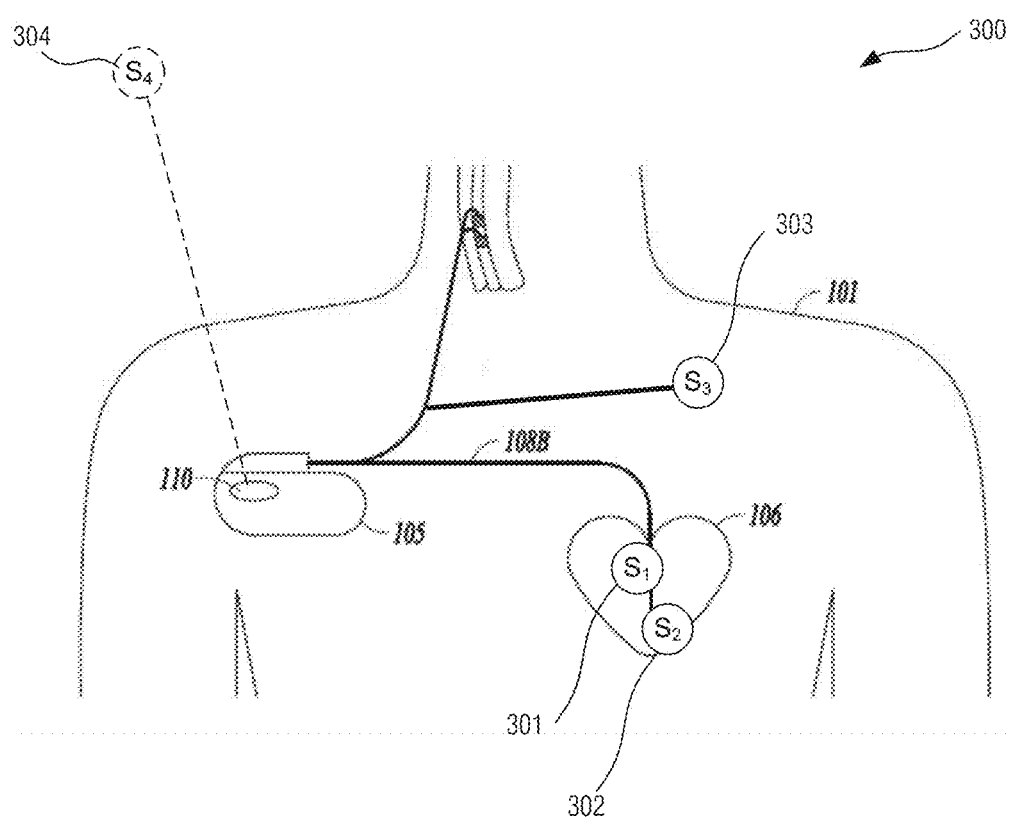
FIG. 3 illustrates generally an example of multiple sensors in a subject body.

Referring now to FIG. 3, the subject body 101 is shown with several physiologic sensors coupled to the IMD 105. In an example, the IMD 105 is coupled to a first sensor 301 (denoted $S_1$), a second sensor 302 (denoted $S_2$), a third sensor 303 (denoted $S_3$), and a fourth sensor 304 (denoted $S_4$). In other examples, the IMD 105 is coupled to as few as one sensor, and in still other examples, the IMD 105 is coupled to two or more sensors.

In the example of FIG. 3, the first sensor 301 is a heart sound sensor (e.g., implemented using the acoustic sensor 201 or the vibration sensor 203), the second sensor 302 is a thoracic impedance sensor (e.g., implemented using the impedance sensor 205), and the third sensor 303 is a pulmonary artery pressure sensor (e.g., implemented using the hemodynamic sensor 204 disposed in a subject pulmonary artery, or implemented using the impedance sensor 205 configured to measure dimensional changes of the subject pulmonary artery, among other). In an example, the fourth sensor 404 is a left ventricle ejection fraction sensor implemented using the processor circuit 110, such as to compute the ejection fraction using information obtained in part from the ECG sensor 202.

Figure 4:
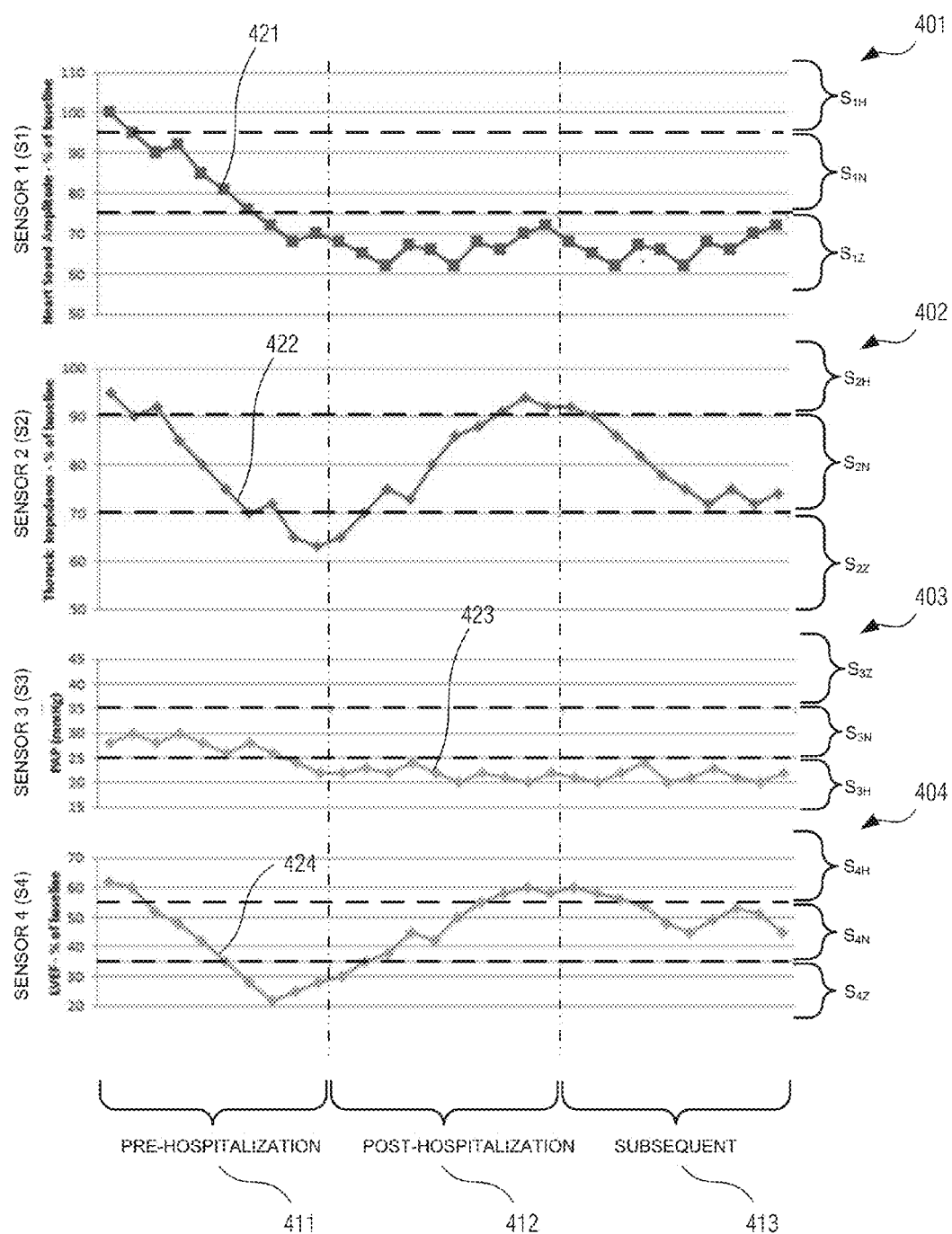
FIG. 4 illustrates generally examples of subject physiologic signals over time.

FIG. 4 illustrates generally examples of charts showing physiologic information received from the sensors illustrated in FIG. 3. The examples in FIG. 4 include first, second, third, and fourth charts 401, 402, 403, and 404, corresponding to physiologic signal information received respectively from the first, second, third, and fourth sensors 301, 302, 303, and 304. In the example of FIG. 4, the sensor information represented in each of the first, second, third, and fourth charts 401, 402, 403, and 404 corresponds to the same time interval along the x axis. The time interval includes a pre-hospitalization period 411 (e.g., a duration before a subject hospitalization or health event), followed by a post-hospitalization period 412 (e.g., a duration during which a subject is undergoing treatment, such as at a hospital), followed by a subsequent period 413 (e.g., a duration after the treatment during the post-hospitalization period 412, such as after discharge from the hospital).

The first chart 401 illustrates generally a first physiologic signal 421 corresponding to a subject heart sound amplitude (e.g., an S1 heart sound amplitude) over time as a percentage of a predetermined baseline heart sound amplitude (e.g., a subject-specific or population-specific baseline, such as normalized to 100%). In the example of the first chart 401, they axis can be divided into several regions corresponding to subject health status inferred from the first physiologic signal 421 information. The first chart includes a first region, $S_{1H}$, corresponding to S1 heart sound amplitudes that represent a healthy subject, a second region, $S_{1N}$, corresponding to S1 heart sound amplitudes that represent borderline, worsening, or neutral subject health status, and a third region, $S_{1Z}$, corresponding to S1 heart sound amplitudes that represent poor subject health status. In an example, when the data from the first physiologic signal 421 corresponds to the third region, $S_{1Z}$, a need for treatment or hospitalization can be indicated. In the example of FIG. 4, the first region, $S_{1H}$, corresponds to heart sound amplitudes that are 95% or more of baseline, the second region, $S_{1N}$, corresponds to heart sound amplitudes between 75% and 95% of baseline, and the third region, $S_{1Z}$, corresponds to heart sound amplitudes below 75% of baseline. The various regions can be subject-specific, such as determined automatically using an algorithm executed by the processor circuit 110, or determined manually by a caregiver. In some examples, the regions are population-specific, or the regions are pre-defined.

In the example of the first chart 401, the first physiologic signal 421 rapidly declines over the pre-hospitalization period 411 from the baseline heart sound amplitude (e.g., where baseline is normalized to 100%) to a minimum heart sound amplitude of about 69%, corresponding to the third region, $S_{1Z}$. In an example, when the first physiologic signal 421 indicates a heart sound amplitude in the third region, $S_{1Z}$, an alert can be provided, such as automatically to the subject or a caregiver, such as using the IMD 105 (e.g., using an audible alert), or using the external system 125 (e.g., using an external interface, such as including a remote patient care management system).

The second, third, and fourth charts 402, 403, and 404, include respective second, third, and fourth physiologic signals 422, 423, and 424. Similarly to the description above regarding the first chart 401, each of the second, third, and fourth charts 402, 403, and 404, include respective regions along they axis that represent different subject health statuses (see, e.g., the second chart 402 at regions $S_{2H}$, $S_{2N}$, $S_{2Z}$, etc.). In the example of FIG. 4, each of the first, second, third, and fourth physiologic signals 421, 422, 423, and 424, indicate hospitalization or treatment for the subject at the end of the pre-hospitalization period 411.

In the example of FIG. 4, at the onset of the post-hospitalization period 412, subject health status is indicated to be poor by each of the first, second, third, and fourth physiologic signals 421, 422, 423, and 424. In an example, the post-hospitalization period 412 includes a treatment event (such as at or near the beginning of the period). Over the course of the post-hospitalization period 412, information from one or more of the sensors can indicate improving subject health status, such as where a corresponding subject physiologic signal trends toward or returns to its baseline.

In the example of FIG. 4, during the post-hospitalization period 412, the first and third physiologic signals 421 and 423 remain in the $S_{1Z}$ and $S_{3Z}$ regions, respectively, corresponding to an indication for further treatment or continued hospitalization. The second and fourth physiologic signals 422 and 424 return to their respective baseline $S_{2H}$ and $S_{4H}$ regions over the same interval, corresponding to improving subject health status. In an example, it can be determined (e.g., automatically by a medical device or manually by a caregiver) that the subject health status is sufficiently improved or stabilized (as indicated by the return of the second and fourth physiologic signals 422 and 424 to baseline), and the subject can be discharged, or the treatment can be terminated. For example, where the treatment event includes administering a pharmacologic diuretic, the diuretic can be discontinued. Subject discharge from the hospital or termination of a therapy can indicate an end of the post-hospitalization period 412. In some examples, other treatments can be provided, such as to address any residual subject health status issues, such as represented by the first and third physiologic signals 421 and 423 which remain at less than optimal levels at the end of the post-hospitalization period 412.

In the example of FIG. 4, at the end of the post-hospitalization period 412, sensors can be identified that correspond to physiologic signals that indicate aspects of a subject physiology that were not responsive to treatment, or that responded negatively to treatment (e.g., by indicating worsening subject health status). Similarly, sensors corresponding to physiologic signals that indicate aspects of a subject physiology that were responsive to treatment can be identified. These sensors can be identified automatically, such as using the processor circuit 110 to analyze the subject physiologic signal information. The sensors corresponding to physiologic signals that were responsive to treatment can be used for subsequent subject health status assessment, such as in the subsequent period 413.

In the example of FIG. 4, during the subsequent period 413, the second and fourth physiologic signals 422 and 424 can be monitored, such as using the processor circuit 110. In the example of the second and fourth charts 402 and 404, the second and fourth physiologic signals 422 and 424 decline from the $S_{2H}$ and $S_{4H}$ baseline regions, respectively. In this example, the second and fourth physiologic signals 422 and 424 decline to the $S_{2N}$ and $S_{4N}$ regions, respectively. These trends away from the signals' respective baseline regions indicate subject health status is declining. In an example, an alert can be provided to a subject or caregiver when one or both of the second and fourth physiologic signals 422 and 424 change by more than a predetermined threshold amount, such as to indicate a possible imminent rehospitalization or a need for a different or adjusted therapy.

In an example, where a particular treatment regimen is initiated during the post-hospitalization period 412 and carried on through the subsequent period 413, the declining health status represented by the second and fourth physiologic signals 422 and 424 over the subsequent period 413 can represent that the particular therapy regimen is losing its effectiveness. In an example, the particular therapy regimen can include a device therapy (e.g., a pacing therapy) that can be automatically or manually updated in response to the change in one or more physiologic signals. In an example, rehospitalization can be indicated in response to the declining subject health status indicated by the second and fourth physiologic signals 422 and 424, such as before the signals reach their respective $S_{2Z}$ and $S_{4Z}$ regions.

In an example, during the subsequent period 413, therapies configured to address the conditions monitored by S2 and S4 can be initiated in response to the declining subject health status indicated by the second and fourth physiologic signals 422 and 424. For example, in FIG. 4, the second physiologic signal 422 represents a subject thoracic impedance relative to a baseline impedance, and is indicative of a subject thoracic fluid level. In response to the decline of the second physiologic signal 422 from about 91% of baseline at the beginning of the subsequent period 413 to about 71% of baseline later in the subsequent period 413 (e.g., indicative of an increase in thoracic fluid level), an operating characteristic of the IMD 105 can be adjusted (e.g., a lower rate limit can be increased) to attempt to reduce the thoracic fluid level. In an example, such a therapy adjustment can be performed automatically by the IMD 105, or can be performed manually by a clinician or other caregiver. In an example, a therapy adjustment can be performed remotely using the external system 125, such as in response to an alert generated by the external system 125 in response to the subject physiologic signals.

Figure 5:
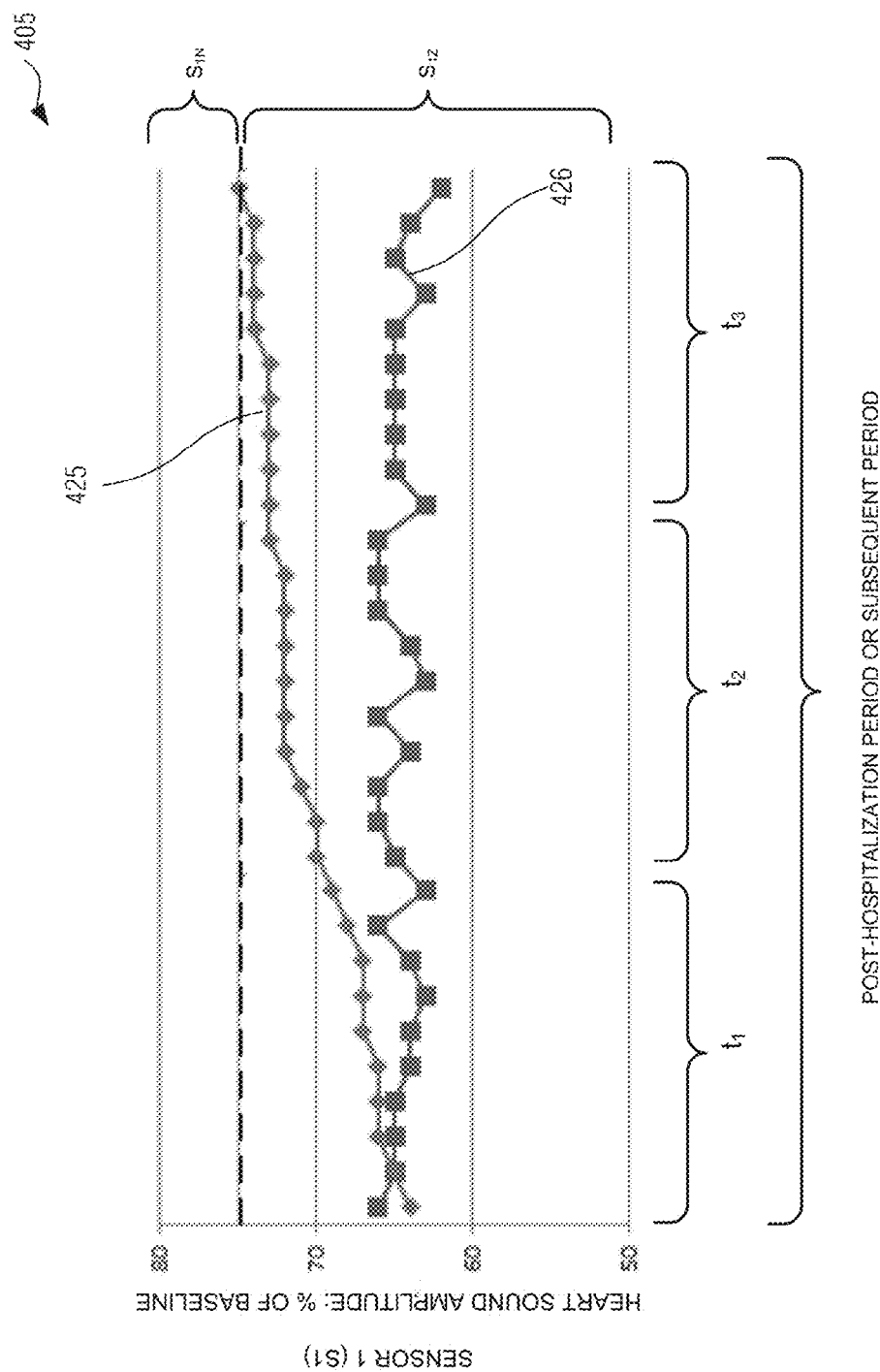
FIG. 5 illustrates generally examples of subject physiologic signals over time.

FIG. 5 illustrates generally an example of a fifth chart 405 corresponding to physiologic signal information received from the first sensor 301. The fifth chart 405 includes fifth and sixth physiologic signals 425 and 426. In the example of FIG. 5, the fifth and sixth physiologic signals 425 and 426 are alternative signals corresponding to different theoretical subject health statuses for a subject over a common time period (e.g., over the post-hospitalization period). In this example, the time period is further divided into equal duration intervals denoted $t_1$, $t_2$, and $t_3$.

In an example, the fifth chart 405 illustrates a post-hospitalization period that includes a subject treatment event (e.g., a pharmacological, device-based, or other therapy or treatment). In an example, the subject physiologic signal over the post-hospitalization period is represented by the fifth physiologic signal 425. In this example, the subject heart sound amplitude improves over the post-hospitalization period, from about 64% of baseline at the beginning of the period to about 75% of baseline at the end of the period. Thus, in this example, the subject heart sound amplitude indicates an improving subject health status as the heart sound amplitude characteristic trends toward the desired 100% of baseline.

In an example, the fifth chart 405 illustrates a subsequent period (e.g., a period following the post-hospitalization period, such as after discharge or after treatment), and the fifth physiologic signal 425 indicates improving subject health status under the therapy or regimen received by the subject over the subsequent period. For example, where a lower rate limit of the IMD 105 was increased in a prior period (e.g., in a post-hospitalization period), the trend of the fifth physiologic signal 425 over the subsequent period can indicate that the lower rate limit adjustment is effective and should be maintained.

In an example, the subject physiologic signal over the post-hospitalization period is represented by the sixth physiologic signal 426. In this example, the subject heart sound amplitude is relatively unchanged over the post-hospitalization period. That is, the sixth physiologic signal 426 begins the post-hospitalization period and ends the post-hospitalization period at about 65% or less of baseline. Because the subject physiologic status is generally expected to improve over the period, the unchanged characteristic of the signal can represent a residual or untreated portion of the subject physiology, and rehospitalization or therapy adjustment can be indicated. Some subject characteristics indicative of an untreated portion of subject heart failure can include unchanged heart sound signal characteristics, unchanged respiration rate, and unchanged tidal volume, among others.

In an example, a subject physiologic signal can be monitored for changes in magnitude by at least a predetermined threshold amount, such as over a specified period. Generally, the information received from a particular physiologic sensor is expected to trend toward its baseline value as subject status improves. However, if information from a particular sensor is static (e.g., the subject physiologic characteristic monitored by the particular sensor remains within a hospitalization range, such as over a specified duration), the subject can be deemed to be not adequately recovering and a risk for subject rehospitalization can be assessed.

In the example of FIG. 5, a rehospitalization alert can be provided when the subject physiologic signal does not improve by the threshold amount over the specified period. In an example, if the subject physiologic signal does not exceed 70% within the first interval $t_1$, then a rehospitalization or other alert can be provided. In this example, because neither the fifth or sixth physiologic signals 425 or 426 exceeds 70% within the first interval $t_1$, a rehospitalization or other alert can be provided. In an example, if the subject physiologic signal does not exceed 70% before the end of the second interval $t_2$, the rehospitalization or other alert can be provided. In this example, the fifth physiologic signal 425 exceeds the threshold amount of 70% before the end of the second interval $t_2$. Accordingly, the alert can be avoided, or withheld for further monitoring. The sixth physiologic signal 426 does not exceed the threshold 70% before the end of the second interval $t_2$, and, accordingly, the alert can be provided.

Figure 6:
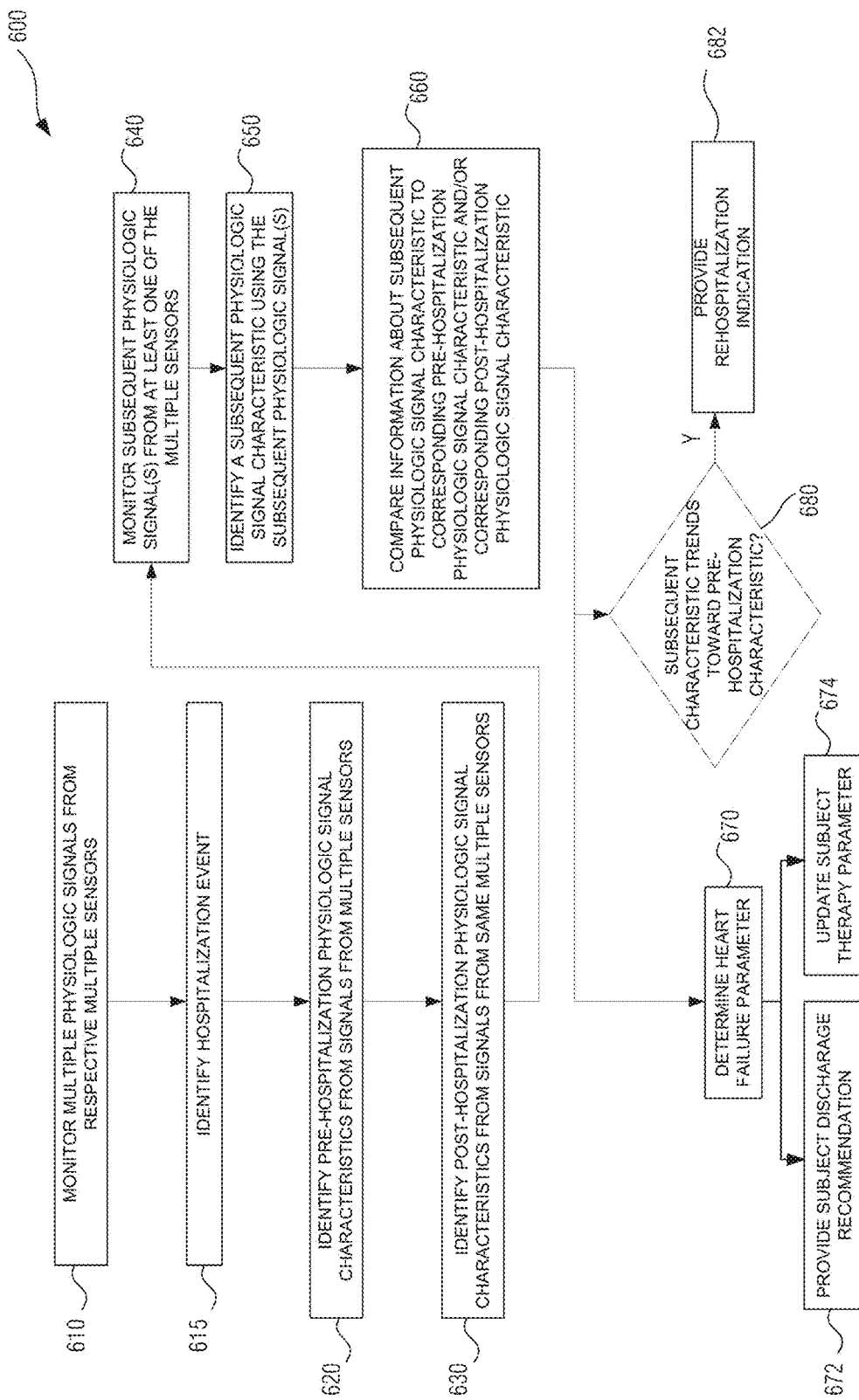
FIG. 6 illustrates generally an example that can include determining a heart failure parameter and providing a rehospitalization indication.

Referring now to FIG. 6, an example 600 includes determining a heart failure parameter and providing a rehospitalization indication. At 610, the example 600 includes monitoring multiple physiologic signals from a subject, over a pre-hospitalization period, using respective multiple sensors. For example, at 610, the monitored physiologic signals can include, among others, heart sound signals, electrophysiologic signals, or hemodynamic signals, such as received from the subject using an acoustic sensor, implanted electrodes, or a pressure transducer, respectively. In an example, the IMD 105 or the external system 125 includes a memory circuit configured to store information about the monitored multiple physiologic signals, such as by periodically sampling a continuous physiologic signal or by using histogram-based storage techniques to store information about a sampled physiologic signal.

At 615, a hospitalization event can be identified. Throughout this document, a hospitalization event refers to any adverse subject health event, such as a heart failure decompensation episode, or other event, episode, symptom, or trend that indicates a subject's health status is declining. For example, a hospitalization event can refer to a time when a heart failure subject seeks treatment for accumulated thoracic fluid. In some examples, a hospitalization event refers to subject admission to a hospital or other treatment facility. In some examples, a hospitalization event refers to an acute or even temporary symptom, such as chest pain or difficulty breathing.

At 620, pre-hospitalization physiologic signal characteristics can be identified. In an example, the IMD 105 or the external system 125 includes a memory circuit configured to store information about recent subject physiologic signal activity from multiple subject sensors. For example, the IMD 105 can include a memory circuit configured to record the last seven days (or more) of subject physiologic signal activity from each of a heart sound sensor and an ECG sensor (e.g., at the same or different sample rates). In response to the hospitalization event identified at 615, the processor circuit 110 can analyze the recorded subject physiologic signals to identify various characteristics of the signals. For example, the processor circuit 110 (or other processing module, such as included in the external system 125) can analyze the recorded heart sound signal and identify an S1 amplitude characteristic over the recorded period. The processor circuit 110 can trend the characteristic information to determine whether the characteristic can be correlated to the hospitalization event or the subject health status. Similarly, the processor circuit 110 can analyze the recorded ECG signal and identify a QRS width characteristic over the recorded period. The QRS width can be analyzed (e.g., automatically by the processor circuit, or by a caregiver) to determine whether the QRS width characteristic can be correlated to the hospitalization event or the subject health status.

At 630, post-hospitalization physiologic signal characteristics can be identified over a post-hospitalization period. The post-hospitalization period corresponds to a period following the hospitalization event. In some examples, the post-hospitalization period includes a period when a subject is at a hospital or other care facility, and in some examples the post-hospitalization period includes a period when a subject is undergoing a treatment regimen (e.g., implemented automatically by the IMD 105 in response to the identified hospitalization event at 615).

At 630, the processor circuit 110 can continue to monitor the subject physiologic signals using the same sensors that were used to receive the pre-hospitalization physiologic signals. Characteristics of the post-hospitalization physiologic signals can be identified, such as characteristics of the same or different type than the characteristics of the pre-hospitalization physiologic signals. For example, the post-hospitalization physiologic signals can include a heart sound signal that can be analyzed to identify S1 amplitude characteristics over the post-hospitalization period. Similarly, the post-hospitalization physiologic signals can include an ECG signal that can be analyzed to identify QRS width information over the post-hospitalization period.

At 640, one or more subsequent physiologic signals can be monitored over a subsequent period, such as using the same multiple sensors used to monitor the multiple physiologic signals at 610. The subsequent physiologic signals can be signals monitored after the post-hospitalization period. In some examples, the subsequent period includes a period after subject discharge from a hospital or other care facility, or the subsequent period includes a period after a subject therapy is updated. For example, the subsequent period can include a period after a lower rate limit of a subject pacemaker device is raised.

In an example, physiologic signal information from a portion of the available subject sensors is used in the monitoring at 640. For example, where a monitored characteristic of a physiologic signal, received from a particular sensor, changes over the post-hospitalization period (e.g., relative to the pre-hospitalization period), subsequent physiologic signal information from that same sensor can be flagged for further monitoring. In an example, signal characteristics that change over the post-hospitalization period can indicate a treatment effect.

At 650, a subsequent physiologic signal characteristic can be identified using the one or more subsequent physiologic signals received over the subsequent period. In an example where the subject heart sound amplitude changes over the post-hospitalization period, the subject heart sound signal can be indicated for further monitoring and analysis over the subsequent period. In an example where the subject QRS duration is shorter over the post-hospitalization period relative to the pre-hospitalization period, the subject ECG signal can be indicated for further monitoring and analysis over the subsequent period. Subsequent characteristics of the heart sound signal and ECG signal, such as monitored over the subsequent period, can be identified at 650.

At 660, information about the subsequent physiologic signal characteristic identified at 650 can be compared to a corresponding pre-hospitalization physiologic signal characteristic or to a corresponding post-hospitalization physiologic signal characteristic. For example, where S1 heart sound amplitude is used, characteristic information about the S1 heart sound amplitude over the subsequent period (e.g., average peak amplitude) can be compared to one or both of the S1 heart sound amplitude from the pre-hospitalization period and the S1 heart sound amplitude from the post-hospitalization period.

In an example, at 670, a heart failure parameter can be determined. The heart failure parameter can be an absolute or relative indication of a subject health status that can be determined using a comparison of physiologic signal characteristics over time. For example, where the characteristic compared at 660 is S1 heart sound amplitude, the heart failure parameter can indicate worsening subject heart failure when the post-hospitalization S1 amplitude characteristic indicates poor subject health status (e.g., S1 amplitude is at 60% of baseline) and the subsequent S1 amplitude characteristic indicates no change from the post-hospitalization period (e.g., S1 amplitude remains at or about 60% of baseline), such as after the subject undergoes treatment or after the subject receives a therapy adjustment.

At 672, a subject discharge recommendation can be provided, such as using the heart failure parameter determined at 670. For example, where the subsequent period includes a period when the subject remains in a care facility, such as after undergoing a medical procedure or receiving a device therapy update, the information about the heart failure parameter determined at 670 can be used to determine or influence a discharge decision. In an example, a discharge alert can be provided automatically using the IMD 105 or the external system 125, or the discharge recommendation can be determined manually by a caregiver, such as in response to the information about the determined heart failure parameter.

At 674, a subject therapy parameter can be updated, such as using the heart failure parameter determined at 670. The therapy parameter update can be performed automatically using the processor circuit 110, or manually by a caregiver who interacts with the external system 125. In an example where the heart failure parameter determined at 670 indicates worsening heart failure, therapy parameters that can be updated at 674 can include a lower or upper pacing rate limit, a diuretic drug administration regimen, a VV delay, an AV delay, an initiation or termination of a neural modulation therapy, or an adjustment to an electrostimulation amplitude, among others.

In an example, at 680, a trend of a subject physiologic signal or signal characteristic can be identified. For example, the subsequent physiologic signal, or a characteristic thereof, can be trended to determine whether the signal or characteristic trends toward a subject pre-hospitalization characteristic, such as described above in the discussion of FIG. 5. In an example, the subsequent physiologic signal or characteristic is trended to identify whether the characteristic is approaching the same level or quantity as was measured when the hospitalization event was identified at 615. In an example where the subsequent physiologic signal or characteristic trends toward the subject pre-hospitalization characteristic, a subject rehospitalization indication can be provided at 682. The subject rehospitalization indication can be provided using the IMD 105 (e.g., using an audible alert) or using the external system 125 to provide an alert to the subject or to a caregiver. The rehospitalization indication can include a risk factor for the subject, based on the trended physiologic signal characteristics, that the subject requires or will require hospitalization.

VARIOUS NOTES & EXAMPLES

Example 1 can include or use subject matter (such as an apparatus, a system, a distributed system, a method, a means for performing acts, or a device readable medium including instructions that, when performed by the device, can cause the device to perform acts), such as can include or use multiple physiologic sensors configured to sense respective physiologic signals from a subject, and a heart failure analysis module. In Example 1, the heart failure analysis module is coupled to the multiple physiologic sensors. In Example 1, the heart failure analysis module includes a processor circuit configured to identify a hospitalization event, and in response to the hospitalization event, perform one or more tasks. For example, in response to the hospitalization event, the processor circuit can be configured to identify pre-hospitalization physiologic signal characteristics corresponding to respective physiologic signals obtained using one or more of the physiologic sensors, identify one or more post-hospitalization physiologic signal characteristics that are different than their corresponding one or more pre-hospitalization physiologic signal characteristics, the one or more post-hospitalization physiologic signal characteristics obtained using the same respective one or more physiologic sensors as the pre-hospitalization physiologic signal characteristics, monitor a subsequent physiologic signal, after the hospitalization event, the subsequent physiologic signal corresponding to one of the one or more post-hospitalization physiologic signal characteristics that are different than their corresponding one or more pre-hospitalization physiologic signal characteristics, the subsequent physiologic signal obtained using the same one or more physiologic sensors as the pre-hospitalization and post-hospitalization physiologic signal characteristics, and identify a subsequent physiologic signal characteristic using the subsequent physiologic signal. In an example, the processor circuit can be configured to determine a heart failure parameter for the subject using information about the subsequent physiologic signal characteristic relative to its corresponding pre-hospitalization physiologic signal characteristic.

Example 2 can include, or can optionally be combined with the subject matter of Example 1, to optionally include the processor circuit configured to update a therapy parameter for the subject using the determined heart failure parameter.

Example 3 can include, or can optionally be combined with the subject matter of one or any combination of Examples 1 or 2 to optionally include the processor circuit configured to determine a parameter indicative of worsening heart failure when the subsequent physiologic signal characteristic trends toward its corresponding pre-hospitalization physiologic signal characteristic.

Example 4 can include, or can optionally be combined with the subject matter of one or any combination of Examples 1 through 3 to optionally include the processor circuit configured to identify the hospitalization event in response to a subject episode. In Example 4, the processor circuit is optionally configured to identify pre-hospitalization physiologic signal characteristics including pre-episode physiologic signal characteristics corresponding respectively to the physiologic signals obtained using one or more of the physiologic sensors.

Example 5 can include, or can optionally be combined with the subject matter of one or any combination of Examples 1 through 4 to optionally include the processor circuit configured to identify the hospitalization event in response to a subject heart failure decompensation episode.

Example 6 can include, or can optionally be combined with the subject matter of one or any combination of Examples 1 through 5 to optionally include the processor circuit configured to provide a rehospitalization indication when the subsequent physiologic signal characteristic trends toward its corresponding pre-hospitalization physiologic signal characteristic.

Example 7 can include, or can optionally be combined with the subject matter of one or any combination of Examples 1 through 6 to optionally include an implantable electrostimulation device coupled to the subject, wherein the processor circuit is configured to determine, based on the determined heart failure parameter, a therapy parameter for a therapy provided by the implantable device to the subject, the therapy parameter including one of an AV delay, VV delay, an upper rate limit, a lower rate limit, a magnitude of an electrostimulation pulse, a duration of an electrostimulation pulse, a shape of an electrostimulation pulse, or a location the electrostimulation pulse is delivered to the subject.

Example 8 can include, or can optionally be combined with the subject matter of one or any combination of Examples 1 through 7 to optionally include, as one of the physiologic sensors, a heart sound sensor configured to provide a heart sound signal. In Example 8, the processor circuit is optionally configured to monitor the heart sound signal, including to identify a pre-hospitalization heart sound amplitude using the heart sound signal and identify a post-hospitalization heart sound amplitude that is different than its corresponding pre-hospitalization amplitude, the processor circuit is optionally configured to monitor, as the subsequent physiologic signal, a subsequent heart sound amplitude using the heart sound sensor, and the processor circuit is optionally configured to determine the heart failure parameter using information about whether the subsequent heart sound amplitude trends toward the pre-hospitalization heart sound amplitude.

Example 9 can include, or can optionally be combined with the subject matter of one or any combination of Examples 1 through 8 to optionally include a heart sound sensor configured to provide a heart sound signal. In Example 9, the processor circuit is optionally configured to monitor the heart sound signal, including to identify, as at least one of the pre-hospitalization physiologic signal characteristics, a pre-hospitalization heart sound timing characteristic using the heart sound signal, the processor circuit is optionally configured to identify, as at least one of the one or more post-hospitalization physiologic signal characteristics, a post-hospitalization heart sound timing characteristic that is different than its corresponding pre-hospitalization timing characteristic, the processor circuit is optionally configured to monitor, as the subsequent physiologic signal, a subsequent heart sound timing characteristic using the heart sound sensor, and the processor circuit is optionally configured to determine the heart failure parameter using information about whether the subsequent heart sound timing characteristic trends toward the pre-hospitalization heart sound timing characteristic.

Example 10 can include, or can optionally be combined with the subject matter of one or any combination of Examples 1 through 9 to optionally include the processor circuit configured to provide a discharge recommendation using the determined heart failure parameter.

Example 11 can include, or can optionally be combined with the subject matter of one or any combination of Examples 1 through 10 to optionally include the processor circuit configured to identify, as the one or more post-hospitalization physiologic signal characteristics that are different than their corresponding one or more pre-hospitalization physiologic signal characteristics, one or more post-hospitalization physiologic signal characteristics indicative of an untreated portion of subject heart failure.

Example 12 can include, or can optionally be combined with the subject matter of one or any combination of Examples 1 through 11 to optionally include the processor circuit configured to identify, as the pre-hospitalization physiologic signal characteristics, baseline physiologic signal characteristics corresponding to the multiple physiologic signals obtained using the one or more physiologic sensors.

Example 13 can include, or can optionally be combined with the subject matter of Example 12, to optionally include the processor circuit configured to determine the heart failure parameter by automatically processing information about the subsequent physiologic signal characteristic relative to its corresponding baseline physiologic signal characteristic.

Example 14 can include, or can optionally be combined with the subject matter of Example 13, to optionally include the processor circuit configured to provide an indication of worsening heart failure when the subsequent physiologic signal characteristic is substantially unchanged or trends away from its corresponding baseline physiologic signal characteristic.

Example 15 can include, or can optionally be combined with the subject matter of Example 14, to optionally include the processor circuit configured to generate a rehospitalization alert using the indication of worsening heart failure.

Example 16 can include, or can optionally be combined with the subject matter of one or any combination of Examples 1 through 15 to optionally include the processor circuit configured to automatically process information about the subsequent physiologic signal characteristic relative to its corresponding pre-hospitalization physiologic signal characteristic during a specified post-hospitalization interval.

Example 17 can include, or can optionally be combined with the subject matter of one or any combination of Examples 1 through 16 to optionally include the processor circuit configured to identify, as one or more of the pre-hospitalization physiologic signal characteristics, the post-hospitalization physiologic signal characteristics, and the subsequent physiologic signal characteristic, respective morphologic signal features, of the same type, of the multiple physiologic signals.

Example 18 can include, or can optionally be combined with the subject matter of one or any combination of Examples 1 through 17 to optionally include an implantable medical device and a memory circuit, coupled to the implantable medical device, wherein the multiple physiologic sensors are coupled to the memory circuit, and the memory circuit is configured to store information about the respective physiologic signals from the subject sensed using the multiple physiologic sensors, and wherein the processor circuit is configured to determine the heart failure parameter using the information stored in the memory circuit, including using information about a pre-hospitalization physiologic signal characteristic.

Example 19 can include, or can optionally be combined with the subject matter of one or any combination of Examples 1 through 18 to include, subject matter (such as an apparatus, a system, a distributed system, a method, a means for performing acts, or a machine readable medium including instructions that, when performed by the machine, that can cause the machine to perform acts), such as can include monitoring multiple physiologic signals obtained using corresponding physiologic sensors, identifying subject-specific baseline characteristics corresponding respectively to the physiologic signals obtained using the physiologic sensors, and identifying a hospitalization event. Example 19 can optionally include, in response to the hospitalization event, one or more of identifying one or more post-hospitalization physiologic signal characteristics that are different than their corresponding baseline characteristics, the one or more post-hospitalization physiologic signal characteristics obtained using the same respective one or more physiologic sensors as the baseline characteristics, monitoring a subsequent physiologic signal, after the hospitalization event, the subsequent physiologic signal corresponding to one of the one or more post-hospitalization physiologic signal characteristics, using the same one or more physiologic sensors for the baseline characteristics and the post-hospitalization physiologic signal characteristics, identifying a subsequent physiologic signal characteristic using the subsequent physiologic signal, and determining a heart failure parameter for the subject using a processor circuit to automatically process information about the subsequent physiologic signal characteristic relative to its corresponding post-hospitalization physiologic signal characteristic and its corresponding baseline characteristic.

Example 20 can include, or can optionally be combined with the subject matter of Example 19, to optionally include updating a device therapy parameter when the subsequent physiologic signal characteristic is substantially unchanged from its corresponding post-hospitalization physiologic signal after a predetermined interval.

Example 21 can include, or can optionally be combined with the subject matter of one or any combination of Examples 1 through 20 to include, subject matter (such as an apparatus, a system, a distributed system, a method, a means for performing acts, or a machine readable medium including instructions that, when performed by the machine, that can cause the machine to perform acts), such as can include multiple physiologic sensors coupled to an implantable medical device and configured to sense respective physiologic signals, and a heart failure analysis module, coupled to the multiple physiologic sensors. In Example 21, the heart failure analysis module optionally includes one or more processor circuits configured to, individually or collectively, receive pre-episode physiologic signal characteristics corresponding to the multiple physiologic signals obtained using one or more of the physiologic sensors, receive one or more post-treatment physiologic signal characteristics that are of the same type and different than their corresponding one or more pre-episode physiologic signal characteristics, the one or more post-treatment physiologic signal characteristics obtained using the same one or more physiologic sensors as the pre-episode physiologic signal characteristics, receive a subsequent physiologic signal, after a hospitalization period that includes a subject treatment, the subsequent physiologic signal corresponding to one of the one or more post-treatment physiologic signal characteristics, the subsequent physiologic signal obtained using the same one or more physiologic sensors as the pre-episode physiologic signal characteristics and the post-treatment physiologic signal characteristics, identify a subsequent physiologic signal characteristic using the subsequent physiologic signal, and update a therapy provided by the implantable medical device using information about the subsequent physiologic signal characteristic relative to its corresponding pre-episode physiologic signal characteristic.

Example 22 can include, or can optionally be combined with the subject matter of one or any combination of Examples 1 through 21 to include, subject matter (such as an apparatus, a system, a distributed system, a method, a means for performing acts, or a machine readable medium including instructions that, when performed by the machine, that can cause the machine to perform acts), such as can include a processor circuit comprising a data input configured to receive physiologic information about a subject using multiple corresponding physiologic sensors, and a data output configured to provide a heart failure parameter for the subject. In Example 22, the processor is optionally configured to monitor multiple physiologic signals obtained using the data input and corresponding physiologic sensors, receive an indication of a hospitalization event, and in response to the hospitalization event, identify pre-hospitalization physiologic signal characteristics corresponding to respective physiologic signals obtained using one or more of the physiologic sensors, identify one or more post-hospitalization physiologic signal characteristics that are different than their corresponding one or more pre-hospitalization physiologic signal characteristics, the one or more post-hospitalization physiologic signal characteristics obtained using the same respective one or more physiologic sensors as the pre-hospitalization physiologic signal characteristics, monitor a subsequent physiologic signal, after the hospitalization event, the subsequent physiologic signal corresponding to one of the one or more post-hospitalization physiologic signal characteristics that are different than their corresponding one or more pre-hospitalization physiologic signal characteristics, the subsequent physiologic signal obtained using the same one or more physiologic sensors as the pre-hospitalization and post-hospitalization physiologic signal characteristics, identify a subsequent physiologic signal characteristic using the subsequent physiologic signal, and determine a relationship of the subsequent physiologic signal characteristic relative to its corresponding pre-hospitalization physiologic signal characteristic to provide the heart failure parameter for the subject.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
 a physiologic sensor configured to sense a physiologic signal from a subject; and
 a heart failure analysis module, coupled to the physiologic sensor, the heart failure analysis module including a processor circuit configured to:
  identify a first physiologic signal characteristic corresponding to the physiologic signal and preceding a hospitalization event;
  receive an indication of a hospital discharge event;
  identify a second physiologic signal characteristic corresponding to the physiologic signal and following the hospital discharge event;
  determine whether the second physiologic signal characteristic is substantially unchanged from the first physiologic signal characteristic; and
  provide a rehospitalization indication when the second physiologic signal characteristic is determined to be substantially unchanged from the first physiologic signal characteristic.

2. The system of claim 1, wherein the processor circuit is configured to provide the rehospitalization indication when, after a specified duration following the hospital discharge event, the second physiologic signal characteristic is determined to be substantially unchanged from the first physiologic signal characteristic.

3. The system of claim 1, wherein the processor circuit is configured to provide the rehospitalization indication when, after a specified duration following the hospital discharge event, the second physiologic signal characteristic does not approach a known baseline signal characteristic for the physiologic signal.

4. The system of claim 1, further comprising an electrical energy delivery circuit configured to generate a electrostimulation therapy for the subject, wherein the processor circuit is configured to adjust the electrostimulation therapy based on the second physiologic signal characteristic being substantially unchanged from the first physiologic signal characteristic.

5. The system of claim 1, wherein the processor circuit is configured to provide the rehospitalization indication when, after a specified duration following the hospital discharge event, the second physiologic signal characteristic trends away from a known baseline signal characteristic for the physiologic signal.

6. The system of claim 1, wherein the physiologic sensor includes a heart sound sensor, and wherein the physiologic signal includes a heart sound signal sensed using the heart sound sensor.

7. The system of claim 1, wherein the physiologic sensor includes a respiration sensor, and wherein the physiologic signal includes a respiration signal sensed using the respiration sensor.

8. The system of claim 1, wherein the physiologic sensor includes a tidal volume sensor, and wherein the physiologic signal includes a tidal volume signal sensed using the tidal volume sensor.

9. The system of claim 1, further comprising at least a second physiologic sensor configured to sense a different physiologic signal from the subject;
wherein the heart failure analysis module is coupled to the second physiologic sensor; and
wherein the processor circuit is configured to withhold the rehospitalization indication when the different physiologic signal substantially corresponds with a known baseline signal level.

10. The system of claim 1, further comprising at least a second physiologic sensor configured to sense a different physiologic signal from the subject;
wherein the processor circuit is configured to receive the indication of the hospital discharge event when the different physiologic signal substantially corresponds to a pre-established baseline signal range for the different physiologic signal.

11. The system of claim 1, comprising an implantable electrostimulation device coupled to the subject, wherein the processor circuit is configured to use the physiologic signal to determine a heart failure parameter and a therapy parameter for a therapy provided to the subject by the implantable device based on the heart failure parameter, the therapy parameter including one of an AV delay, VV delay, an upper rate limit, a lower rate limit, a magnitude of an electrostimulation pulse, a duration of an electrostimulation pulse, a shape of an electrostimulation pulse, or a location for the electrostimulation pulse to be delivered to the subject.

12. The system of claim 1, further comprising an implantable medical device; and
a memory circuit, coupled to the implantable medical device;
wherein the physiologic sensor is coupled to the memory circuit, and the memory circuit is configured to store information about the physiologic signal from the subject sensed using the physiologic sensor; and
wherein the processor circuit is configured to provide the rehospitalization indication using the information stored in the memory circuit, including using information about a pre-hospitalization physiologic signal characteristic.

13. A system comprising:
multiple physiologic sensors configured to sense respective physiologic signals from a subject; and
a heart failure analysis module, coupled to the physiologic sensor, the heart failure analysis module including a processor circuit configured to:
identify a first physiologic signal characteristic corresponding to a first one of the physiologic signals and preceding a hospitalization event, the first physiologic signal characteristic being outside of a first pre-established baseline range;
identify a second physiologic signal characteristic corresponding to a second one of the physiological signals and preceding a hospitalization event, the second physiologic signal characteristic being outside of a second pre-established baseline range;
identify a third physiologic signal characteristic corresponding to the first one of the physiologic signals and indicating a response to a subject therapy following the hospitalization, the third physiologic signal characteristic being within the first pre-established baseline range;
provide a hospital discharge indication based on the indicated response to the subject therapy;
identify a fourth physiologic signal characteristic corresponding to the a second one of the physiologic signals and following the hospital discharge event;
determine whether the fourth physiologic signal characteristic is substantially unchanged from the second physiologic signal characteristic; and
provide a rehospitalization indication when the fourth physiologic signal characteristic is determined to be substantially unchanged from the second physiologic signal characteristic.

14. A method comprising:
monitoring a physiologic signal obtained using a physiologic sensor;
identifying a subject-specific first physiologic signal characteristic corresponding to the physiologic signal and preceding a hospitalization event;
receiving an indication of a hospital discharge event;
identifying a second physiologic signal characteristic corresponding to the physiologic signal and following the hospital discharge event;
determining whether the second physiologic signal characteristic is substantially unchanged from the first physiologic signal characteristic; and
providing a rehospitalization indication when the second physiologic signal characteristic is determined to be substantially unchanged from the first physiologic signal characteristic.

15. The method of claim 14, further comprising monitoring at least one other physiologic signal over an interval between the hospitalization event and the hospital discharge event, wherein the receiving the indication of the hospital discharge event includes in response to identifying a characteristic of the other physiologic signal that trends toward a corresponding baseline characteristic value.

16. The method of claim 14, wherein the providing the rehospitalization indication includes after a specified duration following the hospital discharge event when the second physiologic signal characteristic is determined to be substantially unchanged from the first physiologic signal characteristic.

17. The method of claim 14, wherein the providing the rehospitalization indication further includes after a specified duration following the hospital discharge event when the second physiologic signal characteristic does not approach the first physiologic signal characteristic.

18. The method of claim 14, further comprising identifying a subject-specific baseline characteristic for the physiologic signal;
determining whether the second physiologic signal characteristic is substantially unchanged from the subject-specific baseline characteristic following the hospital discharge event; and
providing the rehospitalization indication when the second physiologic signal characteristic is determined to be substantially unchanged from the subject-specific baseline characteristic following the hospital discharge event.

19. The method of claim 14, further comprising generating a subject therapy, using an implantable medical device, in response to the rehospitalization indication.

20. The method of claim 14, further comprising, in response to the hospital discharge event, identifying a second physiologic signal having a characteristic that changed in response to a therapy administered following the hospitalization event;
   identifying information about a trend of the characteristic of the second physiologic signal following the hospital discharge event; and
   providing the rehospitalization indication based in part on the information about the trend of the characteristic of the second physiologic signal following the hospital discharge event.

\* \* \* \* \*